US006858843B1

(12) United States Patent
Mankos et al.

(10) Patent No.: US 6,858,843 B1
(45) Date of Patent: Feb. 22, 2005

(54) IMMERSION OBJECTIVE LENS FOR E-BEAM INSPECTION

(75) Inventors: Marian Mankos, San Francisco, CA (US); David L. Adler, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/177,394

(22) Filed: Jun. 21, 2002

(51) Int. Cl.⁷ .............................. H01J 3/14; H01J 3/26; G01N 23/00; G21K 7/00
(52) U.S. Cl. ...................... 250/310; 250/306; 250/307; 250/311; 250/396 R; 250/396 ML; 250/397; 250/398
(58) Field of Search .................................. 250/306, 307, 250/310, 311, 396 R, 396 ML, 397, 398, 309, 492.3; 373/13

(56) References Cited

U.S. PATENT DOCUMENTS

| | | | | |
|---|---|---|---|---|
| 3,896,258 A | * | 7/1975 | Hanks | 373/13 |
| 5,598,002 A | * | 1/1997 | Todokoro et al. | 250/310 |
| 5,973,323 A | | 10/1999 | Adler et al. | |
| 6,087,659 A | | 7/2000 | Adler et al. | |
| 6,104,034 A | * | 8/2000 | Frosien et al. | 250/396 R |
| 6,211,518 B1 | * | 4/2001 | Richardson et al. | 250/310 |
| 6,215,128 B1 | | 4/2001 | Mankos et al. | |
| 6,515,287 B2 | * | 2/2003 | Notte, IV | 250/396 ML |
| 6,710,340 B2 | * | 3/2004 | Kazumori | 250/310 |
| 6,720,557 B2 | * | 4/2004 | Frosien | 250/307 |

OTHER PUBLICATIONS

Min Cheng, et al. "Optimization design of immersion magnetic lenses in projection electron beam lithography" International Journal for light and electron optics; Jan. 24, 2001, pp. 149–151; Jiaotong University, P.R. China.
Min Cheng, et al. "Study on wide beam curved optical axes focusing for magnetic immersed lenses without crossovers" International Journal for light and electron optics; May 28, 2000, pp. 509–513; Jiaotong University, P.R. China.
Min Cheng, et al. "Curvilinear–axis focusing and aberration theory of wide electron beams for combined immersion magnetic–electrostatic lens systems" International Journal for light and electron optics; Feb. 5, 2001 pp. 259–267; Jiaotong University, P.R. China.
M. Mankos, et al. "Multisource optimization of a column for electron lithography" J. Vac. Sci. Technology B, Nov./Dec. 2000, pp. 3010–3016, vol. 18, No. 6; Etec Systems, Hayward, California U.S.A.

* cited by examiner

*Primary Examiner*—Frank G. Font
*Assistant Examiner*—Mary El-Shammaa
(74) *Attorney, Agent, or Firm*—Okamoto & Benedicto LLP

(57) ABSTRACT

Disclosed is an apparatus for electron beam inspection of a specimen with improved potential throughput. The apparatus includes an immersion objective lens focusing the primary electrons into a beam that impinges onto a spot on the specimen. Also disclosed is a method for automatic electron beam inspection of a specimen. The method includes producing a magnetic field towards the specimen that reduces aberration towards an outer portion of the multiple pixel imaging region.

3 Claims, 7 Drawing Sheets

IMMERSION OBJECTIVE LENS FOR E-BEAM INSPECTION

BACKGROUND OF THE INVENTION

1. Field of the Invention

The present invention relates generally to specimen inspection. More particularly, the present invention relates to e-beam inspection systems.

2. Description of the Background Art

An example of an electron beam (e-beam) inspection system is shown in FIG. 1 for purposes of background explanation. The secondary electron emission microscope (SEEM) system of FIG. 1 is a projection type system, where a large spot of electrons rather than a small one is formed at the surface of the specimen, and the secondary electrons from this spot are imaged onto a two-dimensional detector. Typically, the specimen may comprise a semiconductor wafer having integrated circuit related structures formed on its surface. Alternatively, the specimen may be another type of sample.

The system of FIG. 1 is described in U.S. Pat. No. 5,973,323, entitled "Apparatus and Method for Secondary Electron Emission Microscope," inventors Adler et al., and assigned at issuance to KLA-Tencor Corporation of San Jose, Calif. The disclosure of U.S. Pat. No. 5,973,323 is hereby incorporated by reference. As described in that patent, FIG. 1 shows the basic configuration for the Secondary Electron Emission Microscopy (SEEM) apparatus. An electron gun source 10 emits a beam 11 of primary electrons $e_1$ along path 12. The electron beam 11 is collimated by electron lens 13 and continues along path 12. Magnetic beam separator 14 then bends the collimated electron beam 11 to be incident along electron optical axis OA normal to the surface to be inspected. Objective electron lens 15 focuses the primary electrons, $e_1$, into a beam having a spot size typically in the range 1–10 mm and an incident energy on the order of 1 keV on specimen 9.

Primary electrons $e_1$ incident on the specimen 9 produce secondary electrons $e_2$ which travel back along the axis OA perpendicular to the inspection surface to objective electron lens 15, where they are re-collimated. Magnetic beam separator 14 bends the electrons to travel along image path 16. The electron beam along image path 16 is focused by projection electron lens 17 to image plane 18, where there is an electron detector 19, which is a camera or preferably a time delay integrating (TDI) electron detector. The operation of an analogous TDI optical detector is disclosed in U.S. Pat. No. 4,877,326, entitled "Method and Apparatus for Optical Inspection of Substrates," inventors Chadwick et al., and assigned at issuance to KLA Instruments Corporation. The disclosure of U.S. Pat. No. 4,877,326 is incorporated herein by reference. The image information may be processed directly from a 'back thin' TDI electron detector 19, or the electron beam may be converted into a light beam and detected with an optional optical system 20 and a TDI optical detector.

FIG. 2 shows parallel imaging in the Secondary Electron Emission Microscopy inspection technique. Beam 54 is produced from an electron gun source, and beam 54 has a width "W," typically about one to two millimeters, at the surface of sample 55. Sample 55 has the characteristic dimension D, which is much greater than the width W of the electron beam. In SEEM, the width of the electron beam 54 is much larger than in secondary electron microscopy (SEM), but it may still be necessary to move the sample 55 with respect to the beam to scan the sample 55. However, in the preferred embodiment, SEEM requires only mechanical movement of the stage of the sample 55 with respect to beam 54, and not an electron beam deflection system for electromagnetically steering beam 41. The SEEM inspection system can operate much faster than the SEM inspection system because SEEM images thousands or millions of pixels in parallel.

FIG. 2 further shows a magnified view of the imaging portion of the beam 54 on the sample 55 to illustrate the parallel, multiple pixel imaging region 56 within beam 54. A rectangular detector array region 56 occupies a central portion of the beam 54 and defines the imaging aperture. (The detector array is either of the time delay integrating (TDI) or non-integrating type.) The detector array 56 may, for example, image between about 500 thousand and one million pixels in parallel.

Despite advances in e-beam inspection, such as SEEM described above, further improvement may be made. For example, it is typically desirable to increase the throughput of an inspection system (the rate at which specimens may be inspected by the system). Factors that limit the throughput of an e-beam inspection system include the usable size and intensity of the beam at the specimen plane. Generally, the larger the usable size of the beam and the higher the usable intensity of the beam, the higher the potential throughput.

SUMMARY

The present invention provides an apparatus and method for electron beam inspection of a specimen with improved potential throughput. The apparatus includes an immersion objective lens focusing the primary electrons onto an area of the specimen while producing a magnetic field towards the specimen. The method includes producing a magnetic field towards the specimen that reduces aberration towards an outer portion of the multiple pixel imaging region.

DETAILED DESCRIPTION

As described above, the usable size and intensity of the beam at the specimen plane may limit the throughput of an e-beam inspection system. Hence, in order to increase the potential throughput of the system, it is desirable to increase the usable beam size and/or intensity.

The present invention uses an immersion objective lens to raise the achievable throughput of e-beam inspection systems. One embodiment of the present invention improves the potential throughput of an SEEM system. The immersion objective lens replaces previously used electrostatic or conventional magnetic objective lenses.

Figure 1:
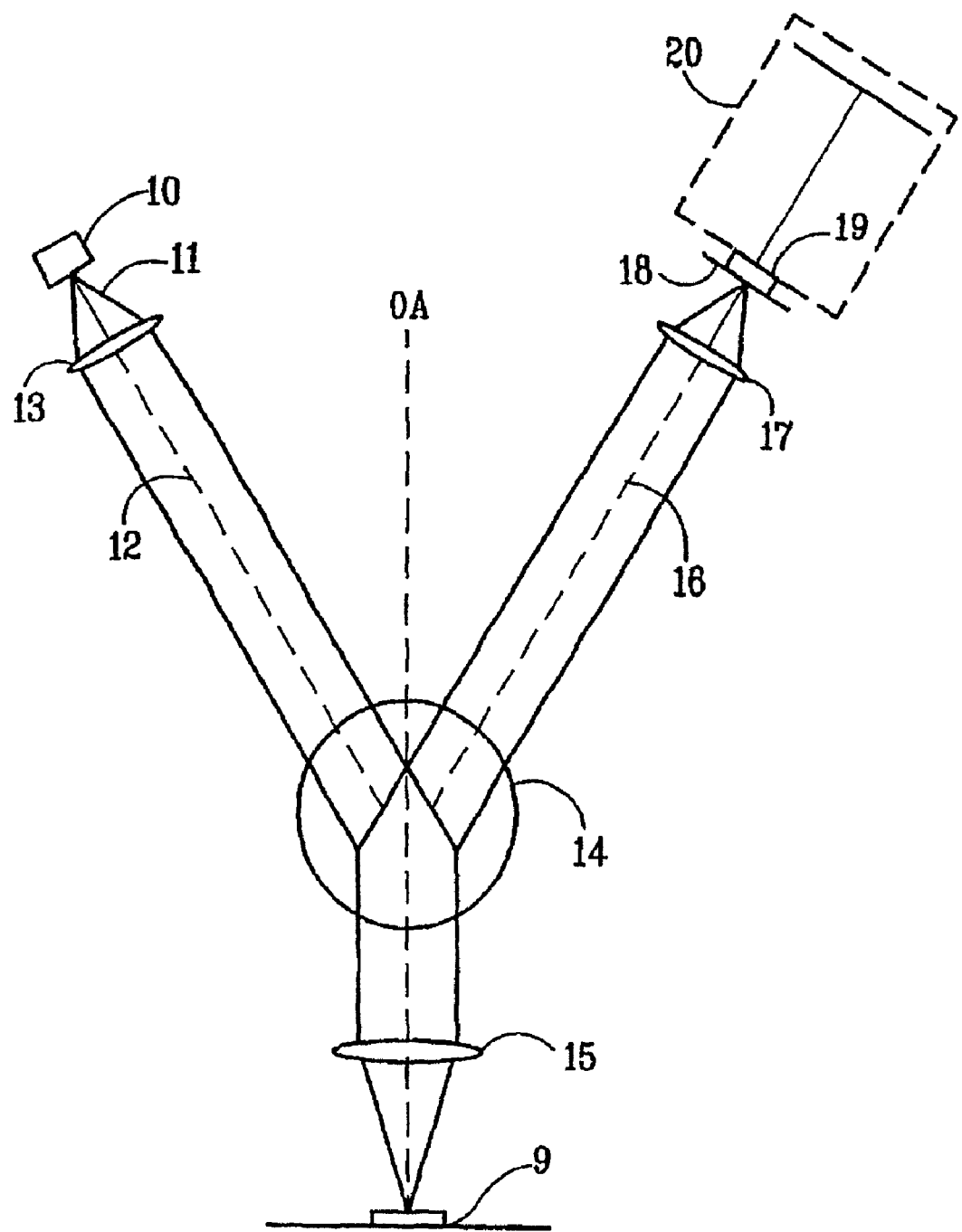
FIG. 1 shows the basic configuration for the Secondary Electron Emission Microscopy apparatus.
Figure 2:
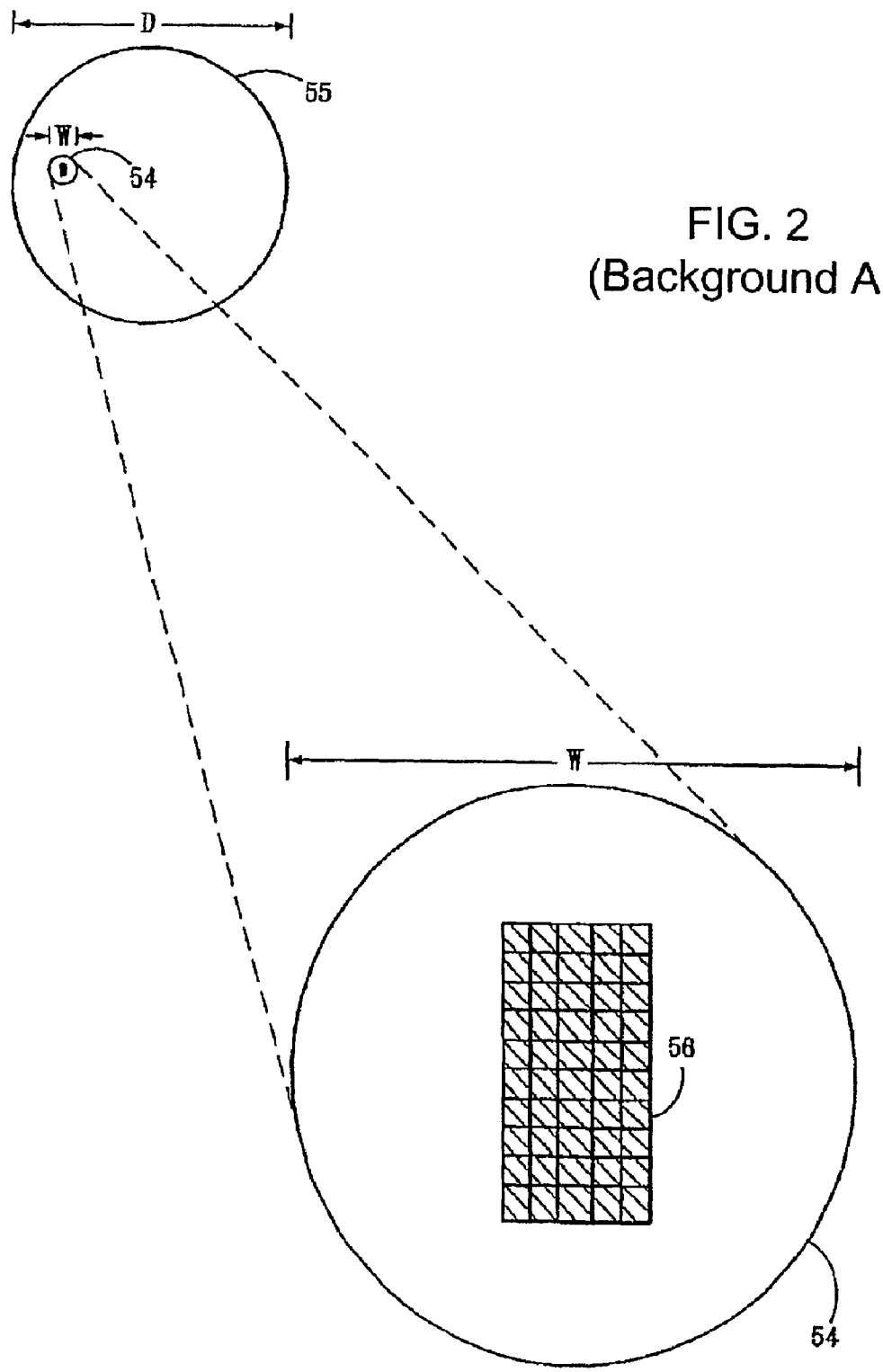
FIG. 2 shows parallel imaging in the Secondary Electron Emission Microscopy inspection technique.
Figure 3:
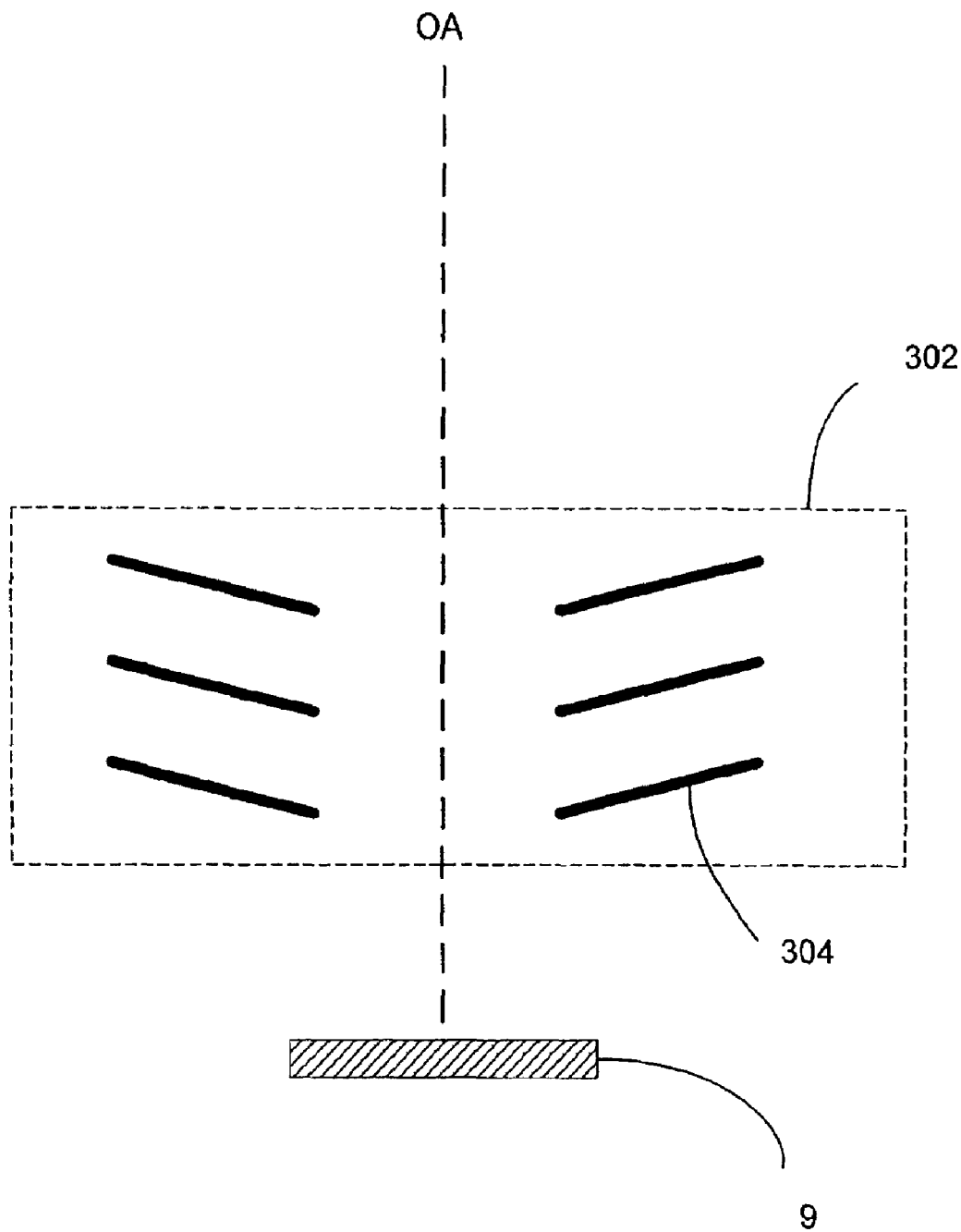
FIG. 3 illustrates a cross-section of an electrostatic objective lens used in an e-beam inspection system.

FIG. 3 illustrates a cross-section of an electrostatic objective lens 302 used in an e-beam inspection system 300. Shown in FIG. 3 are the specimen 9 (corresponding to specimen 9 in FIG. 1) and the electrostatic objective lens 302 (corresponding to the objective lens 15 in FIG. 1). The electrostatic objective lens 302 comprises electrodes 304 that produce an electrostatic field that focuses the e-beam onto an appropriate spot area of the specimen 9.

These previously used electrostatic objective lenses 302 are disadvantageous in that they may cause large aberrations for large imaged areas towards the outer portions of the e-beam. This results in a smaller usable beam size. In addition, electrostatic objective lenses 302 are relatively difficult to mechanically design and implement due to potential electrical arcing between electrodes 304.

Figure 4:
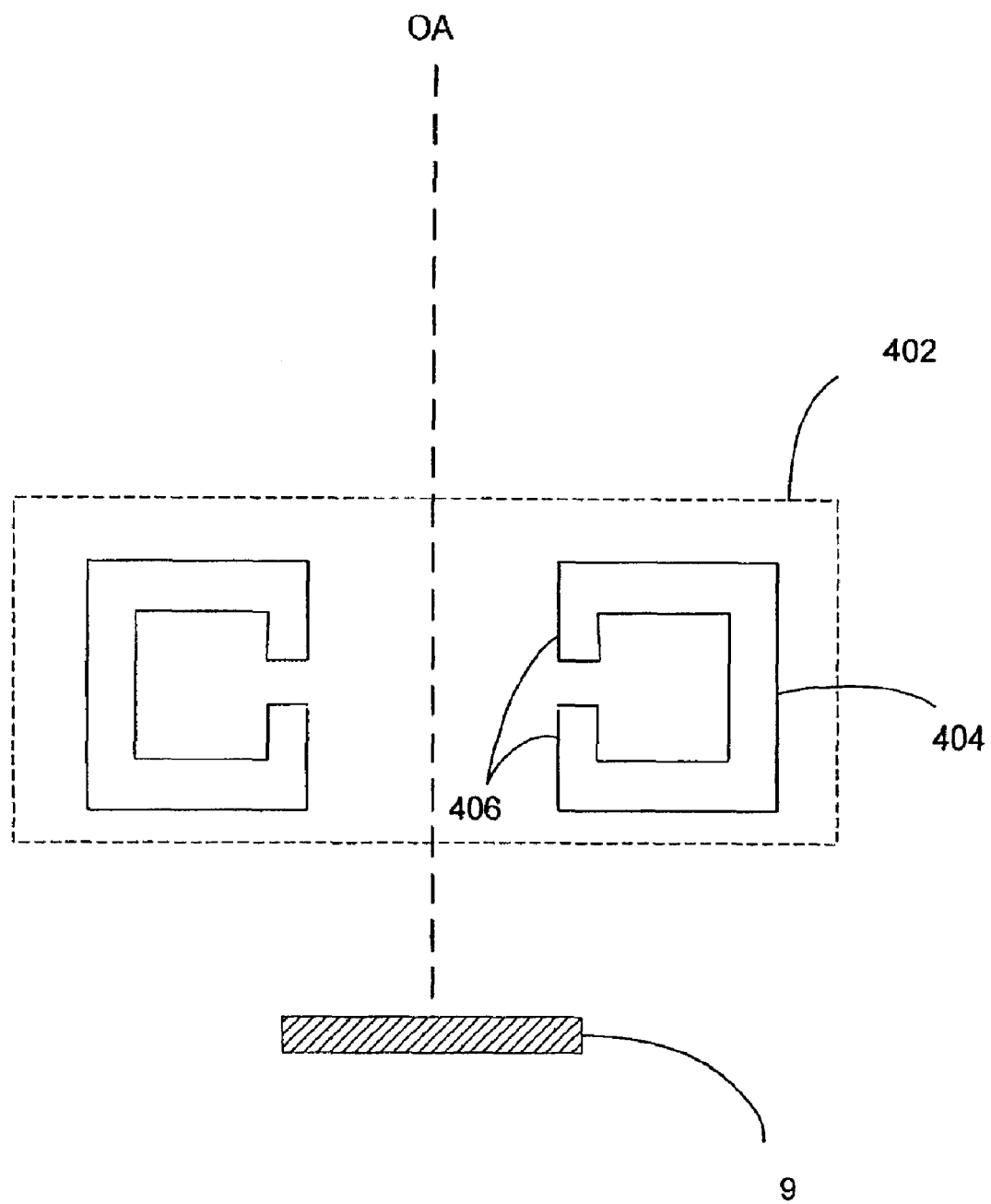
FIG. 4 illustrates a cross-section of a conventional magnetic objective lens used in an e-beam inspection system.

FIG. 4 illustrates a cross-section of a conventional magnetic objective lens 402 used in an e-beam inspection system 400. Shown in FIG. 3 are the specimen 9 and the conventional magnetic objective lens 402 (corresponding to the objective lens 15 in FIG. 1). The conventional magnetic objective lens 402 comprises a current driven electromagnet 404 that produces a magnetic field. The magnetic field is primarily produced from the pole pieces 406 of the electromagnetic structure 404. In conventional magnetic objective lenses 402, the gap between the pole pieces 406 faces the optical axis OA. The magnetic field produced by the electromagnetic structure 404 focuses the e-beam onto an appropriate spot area of the specimen 9.

These previously used conventional magnetic objective lenses 402 cause substantial aberrations for large imaged areas towards the outer portions of the e-beam (although these are typically less than those of a comparable electrostatic objective lens). The aberrations are at least in part due to the divergent action of the acceleration field on the secondary electrons coming from the specimen 9. This divergence of secondary electrons when using a conventional electrostatic lens 302 or a conventional magnetic lens 402 is described further below in relation to FIG. 6.

Figure 5:
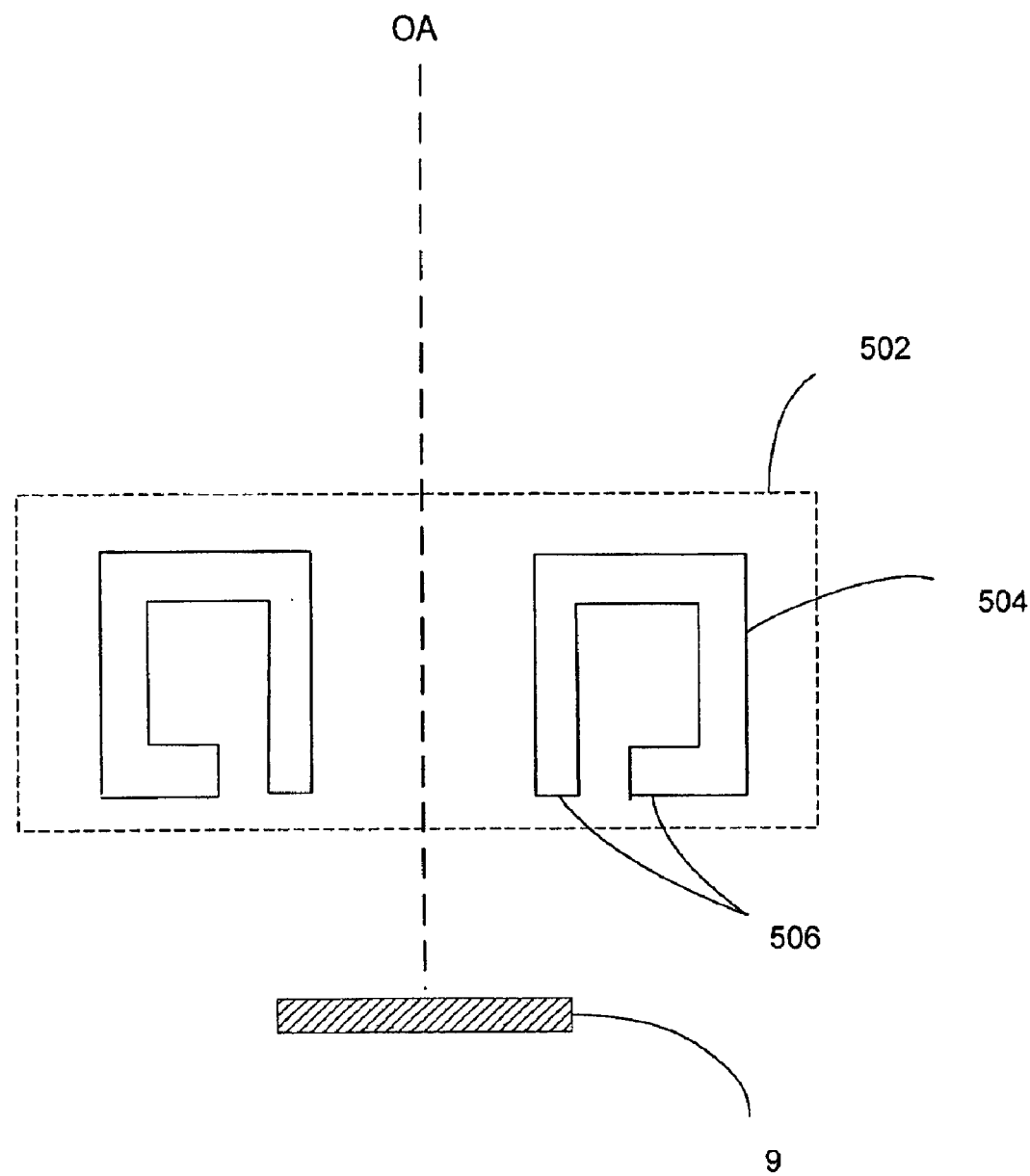
FIG. 5 illustrates an immersion objective lens used in an e-beam inspection system in accordance with an embodiment of the invention.

FIG. 5 illustrates an immersion objective lens 502 used in an e-beam inspection system 500 in accordance with an embodiment of the invention. An immersion objective lens 502 differs from a conventional magnetic objective lens 402 in that the electromagnetic structure 504 has a gap between pole pieces 506 that faces the specimen 9 (instead of facing the optical axis).

The immersion objective lens may comprise a current driven electromagnet 504 that produces a magnetic field. The magnetic field is primarily produced from the pole pieces 506 on the bottom portion of the electromagnetic structure 504. The gap between the pole pieces 506 faces the specimen 9. The magnetic field produced by the electromagnetic structure 504 not only focuses the e-beam onto an appropriate spot area of the specimen 9, but it also immerses the specimen 9 in a magnetic field. In a preferred embodiment of the invention, the electromagnetic structure 504 is axially symmetric about the optical axis, so that the specimen 9 is immersed in a magnetic field that is also axially symmetric about the optical axis.

Advantageously, using an immersion objective lens 502 in the e-beam inspection system 500 reduces the aberration problems that effectively limit the usable spot size of the electron beam. This is because the magnetic field at the specimen 9 reduces the divergence of secondary electrons traveling from the specimen 9. This reduced divergence of secondary electrons when using a immersion objective lens 502 is described further below in relation to FIG. 7.

Figure 6:
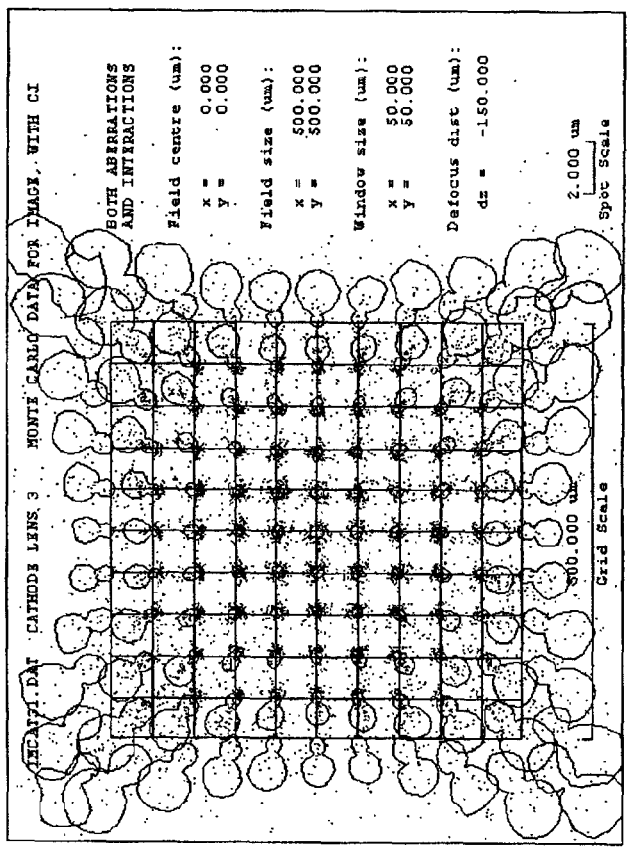
FIG. 6 depicts a simulation of electron trajectories for a system with a conventional electrostatic objective lens.

FIG. 6 depicts a simulation of electron trajectories for a system with a conventional electrostatic objective lens. As shown in FIG. 6, the secondary electrons that are farther away from the optical axis tend to deviate from its intended trajectories, resulting in increased blur and displacement of the beam.

The dots in the diagram represent simulated electrons. One can see that the simulated electrons hit close to the grid intersections (the intended trajectory locations) towards the center of the field (near the optic axis) and are more spread out towards the edge of the field. The closed curves represent regions where the simulated electrons are statistically likely to hit. The regions are tighter around the grid intersections towards the center of the field and are more spread out towards the edge of the field.

Figure 7:
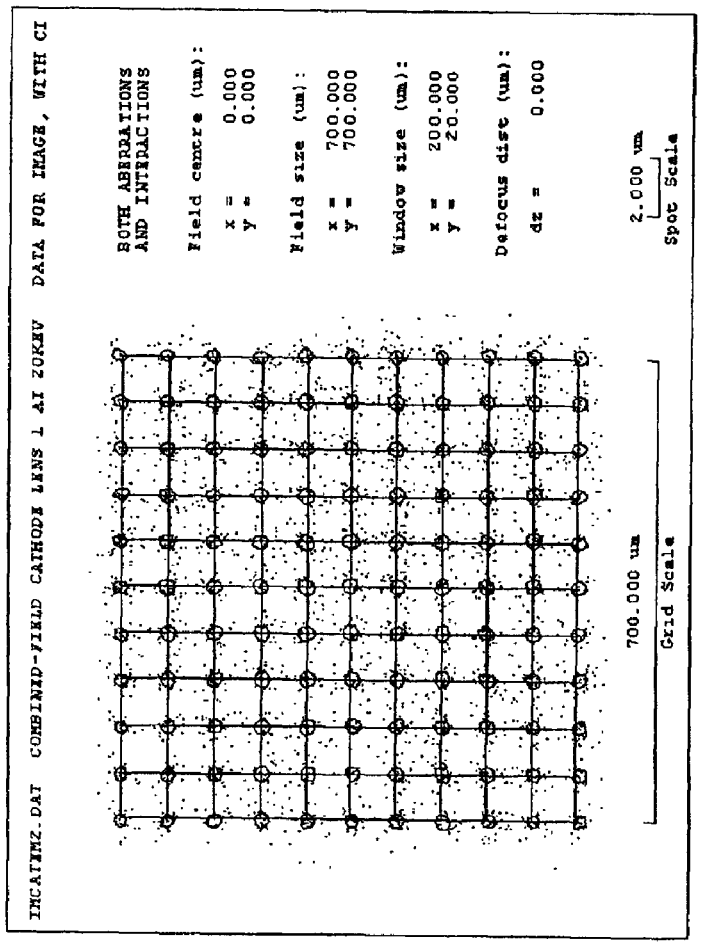
FIG. 7 depicts a simulation of electron trajectories for a system with an immersion objective lens in accordance with an embodiment of the invention.

FIG. 7 depicts a simulation of electron trajectories for a system with an immersion objective lens in accordance with an embodiment of the invention. As shown in FIG. 7, the secondary electrons that are farther away from the optical axis deviate significantly less than the secondary electrons in FIG. 6, resulting in reduced blur and displacement. This is due to the use of the immersion objective lens 502. The immersion objective lens 502 "immerses" the specimen 9 in an axially symmetric magnetic field. The axially symmetric magnetic field causes the secondary electrons to have a spiral component to their motion, and this spiraling lessens the divergence as the secondary electrons travel from the specimen 9.

Again, the dots in the diagram represent simulated electrons, and the closed curves represent regions where the simulated electrons are statistically likely to hit. Here, the simulated electrons hit close to the grid intersections (the intended trajectory locations) throughout the field, and the regions are tighter around the grid intersections throughout the field.

The above-described diagrams are not necessarily to scale and are intended be illustrative and not limiting to a particular implementation. Specific dimensions, geometries, and lens currents of the immersion objective lens will vary and depend on each implementation.

The above-described invention may be used in an automatic inspection system and applied to the inspection of wafers, X-ray masks and similar substrates in a production environment. While it is expected that the predominant use of the invention will be for the inspection of wafers, optical masks, X-ray masks, electron-beam-proximity masks and stencil masks, the techniques disclosed here may be applicable to the high speed electron beam imaging of any material (including perhaps biological samples).

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A projection-type apparatus for electron beam inspection of a specimen, the apparatus comprising:

an electron source for emitting a beam of primary electrons along an optical axis;

a beam splitter to separate the primary electrons from scattered electrons produced by impingement of the primary beam onto the specimen;

an immersion objective lens comprising a current driven electromagnet that projects the primary electrons onto an area of the specimen by producing a magnetic field towards the specimen; and an electron detector for detecting the scattered electrons, wherein the current driven electromagnet comprises a first and a second pole piece, wherein a gap between a first tip of the first pole piece and a second tip of the second pole piece extends away from the optical axis, wherein the area upon which the primary electrons are projected comprises a multiple pixel imaging region, and wherein the electron detector simultaneously detects the scattered electrons emitted from a plurality of pixels within the multiple pixel imaging region.

2. The apparatus of claim 1, wherein the apparatus comprises a secondary electron emission microscope.

3. The apparatus of claim 1, wherein the magnetic field over the area causes the scattered electrons to move spirally in a manner that decreases divergence as the scattered electrons travel from the specimen.

* * * * *